United States Patent [19]

Nakamura et al.

[11] Patent Number: 5,556,760
[45] Date of Patent: Sep. 17, 1996

[54] METHOD FOR ASSAYING UREASE

[75] Inventors: Michihiro Nakamura; Satomi Matsui; Keiko Oka; Hitoshi Tsuruta, all of Kurashiki; Yoshihiro Koori, Fukui-ken; Takuji Kato, Fukui-ken; Shigeji Ito, Fukui-ken, all of Japan

[73] Assignee: Biosensor Research Laboratories Co., Ltd., Tokyo, Japan

[21] Appl. No.: 381,000

[22] Filed: Jan. 31, 1995

[30] Foreign Application Priority Data

Jun. 2, 1994 [JP] Japan ................................. 6-145327

[51] Int. Cl.$^6$ ........................... C12Q 1/58; A61B 5/04
[52] U.S. Cl. ............................. 435/12; 435/4; 128/642; 204/403; 204/433; 604/280; 205/777.5; 205/787.5
[58] Field of Search ........................ 435/12, 4; 128/642, 128/662.03, 662.06; 204/153.21, 403; 424/94.6; 604/280

[56] References Cited

U.S. PATENT DOCUMENTS

| | | | |
|---|---|---|---|
| 3,888,237 | 6/1975 | Mori | 128/E 2 |
| 4,381,011 | 4/1983 | Somers | 128/635 |
| 4,774,956 | 10/1988 | Kruse | 128/635 |
| 4,947,861 | 8/1990 | Hamilton | 128/719 |
| 5,158,083 | 10/1992 | Sacristan | 128/635 |
| 5,262,156 | 11/1993 | Alemohammad | 424/92 |
| 5,292,344 | 3/1994 | Douglas | 607/40 |
| 5,314,804 | 5/1994 | Boguslaski et al. | 435/12 |

FOREIGN PATENT DOCUMENTS 9319200  9/1993  WIPO .

OTHER PUBLICATIONS

Yamamoto, I., Detection of H. Pylori by Urease Teat and Urga Breath Test, Rinshou Shoukari–Naira vol. 8, No. 4, 1993 pp. 517–524, See Abstract.

Rinshou Shoukaki–naika, vol. 8, No. 4, 1993, pp. 489–494, Kyoichi Kobashi, "Helicobacter Pylori Urease And Mucosal Damage Induced By Ammonia" (with English abstract).

Rinshou Shoukaki–naika, vol. 8, No. 4, 1993, pp. 503–510, Eiji Ishii, "Recent Features of Histological And Bacteriological Detections Of Helicobacter Pylori" (with English abstract).

Rinshou Shoukaki–naika, vol. 8, No. 4, 1993, pp. 551–516, Atsushi Takagi, "Serodiagnosis Of Helicobacter Pylori Infections" (with English abstract).

Rinshou Shoukaki–naika, vol. 8, No. 4, 1993, pp. 517–524, Issei Yamamoto, et al., "Detection Of Helicobacter Pylori By Urease Test And Urea Breath Test" (with English abstract).

Rinshou Shoukaki–naika, vol. 8, No. 4, 1993, pp. 525–532, Yoshihiro Kohli, et al., "Phenol Red Dye Spraying Endoscopy" (with English abstract).

Butcher, et al. "Use of an ammonia electrode for rapid quantification", Digestion, vol. 53, No. 3–4, Dec. 1992 Basel, pp. 142–148.

*Primary Examiner*—Ralph J. Gitomer
*Attorney, Agent, or Firm*—Oblon, Spivak, McClelland, Maier & Neustadt, P.C.

[57] ABSTRACT

A method for assaying an enzyme on a targeted solid body surface, including the steps of contacting an end opening of a thin tube with a targeted solid body surface to form a space between the targeted solid body surface and inner wall surface of the thin tube, supplying a substrate solution into the space to bring the substrate solution in contact with the targeted solid body surface, and determining a pH change of the substrate solution in the space by using a pH electrode; and an apparatus therefor.

7 Claims, 3 Drawing Sheets

METHOD FOR ASSAYING UREASE

BACKGROUND OF THE INVENTION

1. Field of the Invention

The present invention relates to a method for assay of an enzyme and an apparatus therefor. More specifically, the present invention relates to a method for assay of an enzyme in which an enzyme on a solid body surface is assayed by measuring a pH change of a substrate solution that occurs depending on the activity of the enzyme on a solid body surface; and to an apparatus suitably used for the method. The method for assay of an enzyme of the present invention is mainly used in the field of clinical laboratory examinations, but it is also applicable to such fields as experimental medicine, veterinary medicine, biochemistry, and pharmacology.

2. Discussion of the Related Art

In recent years, *Helicobacter pylori* (hereinafter referred to as "*H. pylori*") has drawn attention as a bacterium involved in the onset of gastric ulcer and duodenal ulcer. *H. pylori*, which is found in the mucosal epithelia of the stomach and the duodenum, is reported to decompose urea in the stomach and the duodenum by a large amount of urease it expresses on its membrane or secretes extracellularly. This produces a high concentration of ammonia and creates a neutral environment suitable for the growth of *H. pylori*, which injures epithelial cells of the organs [Kohashi, *Rinsho Shokaki Naika*, 8, 489 (1993)]. Therefore, *H. pylori* testing has increasingly become important for diagnosis of gastric and duodenal ulcers.

There are several practical methods for testing *H. pylori* in the stomach and the duodenum (hereinafter referred to as "the gastrointestinal tract"), including (1) culturing, (2) tissue staining, (3) the rapid urease test, (4) endoscopic method using dyes, and (5) the antibody test [Ishii, *Rinsho Shokaki Naika*, 8, 503 (1993)].

Of the existing methods (1) to (5) above, the culturing method (1) is to detect *H. pylori* by isolation culture, etc. using a mucosal tissue specimen. Although this method can give the most reliable results, it injures patient's organ because a mucosal tissue specimen should be obtained. The culturing method also requires skilled operation and takes several days. The tissue staining method (2) also requires collection of a mucosal tissue specimen and therefore injures patient's organ. It also requires skilled operation and takes about one day. In the rapid urease test (3), a mucosal tissue specimen is collected and placed in a medium containing urea and an indicator (e.g., phenol red), and a pH changes of the medium caused by urease secreted by *H. pylori* are visualized by an indicator [Yamamoto et al., *Rinsho Shokaki Naika*, 8, 517 (1993)]. Although results can be obtained within several minutes to hours with simple operation, this method, like methods (1) and (2), needs to collect mucosal specimen and injures the organs. The endoscopic method using a dye (4) is to visually observe the distribution of *H. pylori* in the gastrointestinal tract with an endoscopy after spreading the urea solution containing an indicator, such as toluidine blue or phenol red, in the gastrointestinal tract [Kori et al., *Rinsho Shokaki Naika*, 8, 525 (1993)]. Although this method is advantageous in that *H. pylori* distribution in the gastrointestinal tract can be observed without injuring patient's organ, it is necessary to adjust the gastrointestinal pH near the color change range in advance by, for example, administering an $H_2$ blocker, because the color change range of an indicator is limited, and false-positive or false-negative responses may occur if the pH is not adjusted appropriately. The antibody test (5) is to determine anti-*H. pylori* antibodies in serum by enzyme immunoassay [Takagi, *Rinsho Shokaki Naika*, 8, 511 (1993)]. Because this method measures antibodies against *H. pylori*, rather than *H. pylori* itself, it assesses past history of *H. pylori* infection, and is incapable of determining whether or not *H. pylori* is present in the patient body.

As stated above, there are various methods for testing *H. pylori*, each having both advantages and disadvantages. From the clinical viewpoint, required is a method that can detect *H. pylori* in situ at a targeted site of the gastrointestinal tract at the time of endoscopy without sampling tissue specimens. Such direct in situ detection method is also desired for detecting other microorganisms in various organs, because at present bacteriological approaches, which comprise specimen sampling, in vitro culturing and microscopic observation, are used in most cases. Further, there is also a great practical need for direct measurement of an enzyme at a targeted site of an organ or solid culture medium, because collection of specimens should be unavoidable in most existing assays of enzymes.

SUMMARY OF THE INVENTION

The present invention has been developed to give a solution to the above subject. Specifically, the object of the present invention is to provide a method and an apparatus for directly assaying an enzyme at a targeted site on the surface of a solid body, such as an organ and a solid culture medium, and thereby make it possible to directly detect microorganisms, etc. residing at targeted sites on the solid body surface in situ.

In summary, the present invention relates to: (1) A method for assaying an enzyme on a targeted solid body surface, comprising contacting an end opening of a thin tube with a targeted solid body surface to form a space between the targeted solid body surface and inner wall surface of the thin tube; supplying a substrate solution into the space to bring the substrate solution in contact with the targeted solid body surface; and determining a pH change of the substrate solution in the space by using a pH electrode comprising a sensing portion whose tip is arranged in the space to be not more than 5 mm away from the end opening of the thin tube; (2) An apparatus for assaying an enzyme on a targeted solid body surface based upon a pH change of a substrate solution caused by a reaction of the substrate catalyzed by the enzyme, the apparatus comprising (a) a thin tube; (b) a pH electrode housed in the thin tube, comprising a sensing portion whose tip is arranged in the thin tube to be not more than 5 mm away from an end opening of the thin tube; and (c) a liquid supply means which supplies a substrate solution to the end opening of the thin tube.

The term "solid body" is used to refer to an object having a distinct surface shape, such as the stomach, duodenum, small intestine, large intestine, rectum, urethra, oviduct, bronchium, gingiva and other organs, or a solid culture medium. The term "reaction of the substrate" used herein refers to a wide variety of reactions catalyzed by enzymes, etc., including decomposition, oxidation, reduction, transfer, hydrolysis, elimination, isomerization and polymerization.

BRIEF DESCRIPTION OF THE DRAWINGS

The objects and features of the invention may be understood with reference to the following detailed description given hereinbelow and the accompanying drawings which are given by way of illustration only, and thus, are not limitative of the present invention, and wherein.

Figure 1:
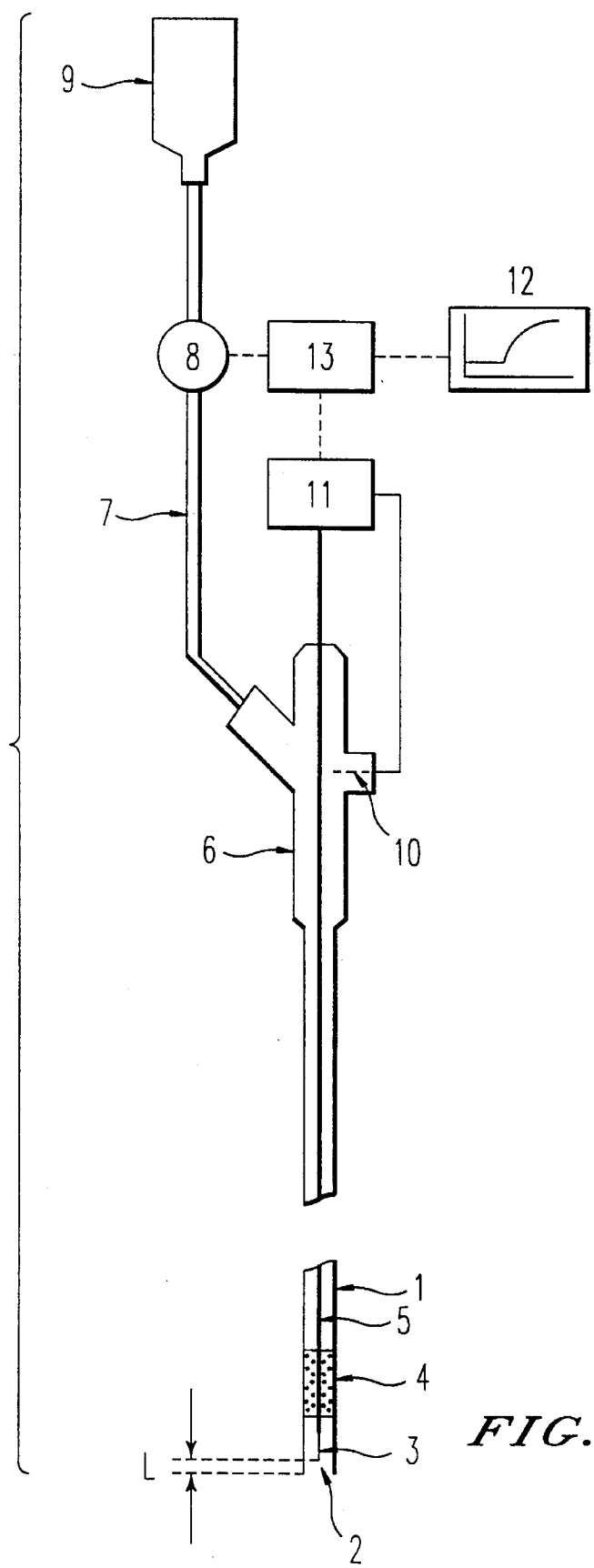
FIG. 1 is a schematic diagram of one preferred embodiment of the apparatus of the present invention.

The reference numerals in FIGS. 1 through 6 denote the following elements:

Element 1 is a thin tube; element 1', a first thin tube; element 1", a second thin tube; element 2, a thin tube opening; element 3, a pH electrode; element 4, a holder; element 5, a lead wire portion; element 6, an adapter; element 7, a liquid supply tube; element 8, a liquid supply means; element 9, a liquid reservoir; element 10, a reference electrode; element 11, a pH electrode output potential reader; element 12, a display; element 13, a computer; element 14, a screw portion; element 15, a fixing portion; element 16, a substrate solution flow path; and element 17, a solid body.

DETAILED DESCRIPTION OF THE INVENTION

The apparatus of the present invention is hereinafter described with reference to drawings.

FIG. 1 illustrates a schematic diagram of one preferred embodiment of the apparatus of the present invention. The apparatus comprises a thin tube 1, a pH electrode 3, and a liquid supply means 8 for supplying a substrate solution into the thin tube 1. Numerical symbols 4 and 5 denote a pH electrode holder and a lead wire portion, respectively; the lead wire connecting to the pH electrode 3 and the soldered portion thereof are sealed with insulating resin. Numerical symbols 9, 10 and 11 denote a liquid reservoir for a substrate solution, a reference electrode, and a pH electrode output potential reader, respectively. Numerical symbol 13 denotes a computer which controls the liquid supply means 8, processes the data read by the output potential reader 11 and shows the processed data on a display 12.

The thin tube 1 has a thin tube opening 2 at one end and connects to an adapter 6 at the other end. The thin tube 1 communicates with the liquid supply tube 7 via the adapter 6 and further communicates with the liquid reservoir 9 via the liquid supply tube 7. The thin tube 1 may have any shapes, as long as it is long and tubular. It may take the form of an endoscopic tube, a catheter or an indwelling needle. The thin tube 1 may be a number of tubes connected in series.

Materials suitable for the thin tube 1 include plastics such as polytetrafluoroethylene, polyvinyl chloride, polypropylene, polyethylene, polyamide, polycarbonate, and polymethyl methacrylate; metals such as stainless steel, aluminum, and titanium; and ceramics. For assay of an enzyme at a targeted site on the surface of an organ, it is preferable that the thin tube 1 be made of a flexible material, such as a plastic.

The inside diameter of the thin tube 1 is usually not more than 3 mm. When the inside diameter is not more than 3 mm, the response of the pH electrode is particularly favorable. However, though the response of the electrode becomes less sensitive, acceptable response can still be obtained even when the inside diameter exceeds 3 mm. Although the lower limit of the inside diameter of the thin tube 1 is not subject to limitation, it can be limited by the outside diameter of the pH electrode housed therein. Practically, the inside diameter of the thin tube 1 usually ranges from 0.5 to 3 mm.

The outside diameter of the thin tube 1 is usually from 0.7 to 4 mm. For enzyme assay at a targeted site on the organ surface, it is desirable that the outside diameter be not more than 3.5 mm in order that the thin tube 1 can be inserted into an endoscope and does not give much burden to a patient upon insertion of the endoscope.

In addition to glass electrodes that have most commonly used, various micro-electrodes for pH may be used as the pH electrode 3 housed in the thin tube 1, including pH-sensitive field-effect transistors (hereinafter referred to as pH-FET), pH electrodes of surface-oxidized metal wire type such as palladium oxide/palladium wire, and pH electrodes of the coated wire type in which a metal wire or a carbon wire is coated with a pH-sensitive polymer membrane having a proton receptor. However, pH electrodes other than pH-FET have some defects. A glass electrode tends to increase inductive noise as it is thinned. A pH electrode of surface-oxidized metal wire type can easily be thinned, but it is faulty with respect to long-term service in water. A pH electrode of the coated wire type can also be thinned easily, but it has problems of narrow linear response range to pH changes and short service life in water. Therefore, in order for these pH electrodes to be used suitably for the present invention, problems as mentioned above should be solved before use.

On the other hand, pH-FET is most suitably used for the present invention for the following reasons: (1) it can easily be thinned; (2) significant inductive noise due to thinning does not occur; (3) being manufactured by IC technology, pH-FETs show minimal variations in electrode characteristics among products and can have the pH sensing surface (gate) miniaturized; (4) response to pH changes is very rapid, with no hysteresis on the response curve; (5) the linear response range for pH changes is wide; and (6) storage stability in water is semi-permanent, with little changes in pH sensitivity and other properties during long service duration. With these excellent features, pH-FET is suitably used as a pH electrode in the apparatus of the present invention.

There are several types of pH-FET, including (1) the entire periphery insulation type (see Japanese Patent Examined Publication No. 57-43863), (2) the junction separation type (see Japanese Utility Model Examined Publication No. 58-5245) and (3) the SOS type (see Japanese Patent Laid-Open No. 59-48646). Although any of these types can be used for the present invention, it is preferable for a pH-FET used in the present invention to meet the following basic requirements: (1) a pH-sensing face positions close to the electrode tip, (2) when a lead wire is connected to a pH-FET and insulated with resin, etc., the insulated portion has a diameter small enough to be inserted into the thin tube 1, (3) the elemental device's tip is 1 to 10 mm, preferably 1 to 3 mm in length, and (4) all the upper, lower and side faces of the elemental device's tip are electrically insulated from the outside solution. In the present invention, pH-FET of the entire periphery insulation type (1) above is preferred, because it meets all the above requirements.

The pH-FET for the present invention desirably has a pH sensitivity of 40 to 60 mV/pH, preferably 50 to 60 mV/pH at 25° C. It is also preferable that the pH-sensing membrane be of a material having excellent stability in water, such as silicon nitride, aluminum oxide and tantalum oxide. Tantalum oxide, in particular, is excellent in stability in water, response to pH, and other properties. Thus, a pH-FET with a pH-sensing membrane of tantalum oxide is suitably used as a pH electrode in the present invention.

When an enzyme is assayed by using the apparatus of the present invention, a pH-FET used for the apparatus should desirably have an extremely low level of noise (not higher than 0.05 mV at a constant pH). Therefore, it is desirable that the mutual conductance of the pH-FET be not less than 50 microsiemens, preferably not less than 100 microsiemens, and more preferably not less than 200 microsiemens. Also, the leak current is desirably not more than 30 nA, preferably not more than 10 nA, when a 3 V voltage is applied between the source electrode of pH-FET and an outside electrode, with the pH-FET elemental device's tip and outside electrode being immersed in physiological saline at room temperature. If the mutual conductance is less than 50 microsiemens, or if the above-described leak current exceeds 30 nA, assay noise becomes significant.

The reference electrode 10 may be a liquid junction type reference electrode, such as a saturated calomel electrode; a silver-silver chloride electrode; a field-effect transistor with an ion-insensitive membrane as a gate membrane (see Japanese Patent Examined Publication No. 58-25221); and a coated wire type reference electrode where a metal wire or a carbon wire is coated with an ion-insensitive membrane. Although the reference electrode used in the apparatus of the present invention may be of any type, a liquid junction type reference electrode is preferably used, because it is highly reliable. The reference electrode is usually housed in the adapter 6 such that it is in liquid junction with the pH-sensing face of the pH electrode as illustrated in FIG. 1, the reference electrode can be placed at any site as long as it is in liquid junction with the pH-sensing face of the pH electrode. For example, the reference electrode may be housed in the thin tube 1 or liquid supply tube 7.

The liquid supply means 8 for supplying a substrate solution into the thin tube 1 may be of any one, as long as it provides a flow rate of from 1 to 100 ml/hr, and conventional liquid supply means, such as peristaltic pumps and syringe pumps, can be used without limitation.

The holder 4, housed in the thin tube 1, keeps the pH electrode 3 at a particular position in the thin tube. The holder 4 is attached and fixed to both the lead wire portion 5 of the pH electrode and the inner wall of the thin tube 1 with an adhesive.

The holder 4 has flow paths for a substrate solution. The holder 4 is made of a porous material, such as a porous sponge, porous ceramic or sintered metal powder.

By the holder 4 above, the pH electrode 3 is accommodated and fixed at a particular position in the thin tube. The position of the pH electrode 3 is an important factor that determines the response rate of the pH electrode to the reaction of substrate. In the assay method and the apparatus of the present invention, the pH electrode 3 preferably takes a position such that the tip of the pH-sensing portion is in the thin tube 1, while keeping a distance (L in FIG. 1) of not more than 5 mm from the thin tube opening 2.

When the apparatus of the present invention is used, the thin tube opening 2 is brought into contact with the surface of a subject solid body to form a space between the solid body surface and the inside wall of the thin tube, and pH changes of the substrate solution in the space are measured using a pH electrode. Since the measuring apparatus of the present invention detects pH changes due to a reaction which takes place on the solid body surface between the enzyme and the substrate in the substrate solution in the space by means of the pH electrode, it is preferable that the distance between the pH-sensing portion of the pH electrode and the solid body surface be kept as small as possible, and that the distance L between the tip of the pH-sensing portion and the thin tube opening 2 be as small as possible. If this distance L exceeds 5 mm, the pH electrode response to the substrate reaction is delayed. If the tip of the pH-sensing portion is exposed from the thin tube opening 2, the pH-sensing portion comes in direct contact with the solid body surface. This not only damages or contaminates the electrode, but also affects liquid sealing of the above-described space formed at the time of enzyme assay. Thus, the substrate reaction and pH changes of the solution in the space can externally be affected, and thereby accurate enzyme assay is hampered. The distance L between the pH-sensing portion tip and the thin tube opening is normally 0.1 to 5 mm, preferably 0.1 to 1.0 mm.

Figure 2:
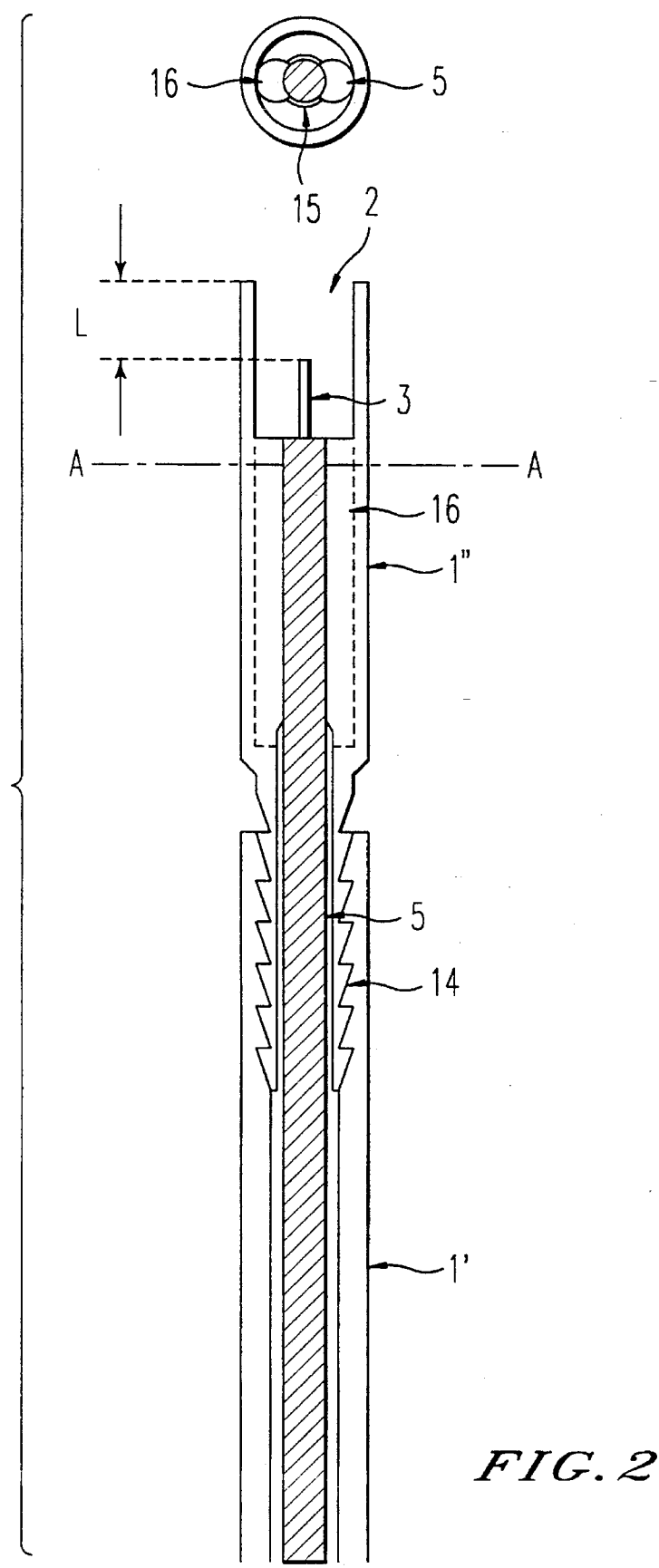
FIG. 2 is a schematic diagram of a thin tube end of another preferred embodiment of the apparatus of the present invention (lower) and a sectional view taken along line A—A (upper).

FIG. 2 shows another embodiment of the apparatus of the present invention. In this embodiment, the thin tube 1 comprises a first tube 1' and a second tube 1", the second tube 1" connecting to one end of the first tube 1' via a screw portion 14. The second tube 1" houses an fixing portion 15 which holds the lead wire portion 5 inserted therein and fixes the position of the pH electrode 3 connected at the end of the lead wire. If necessary, an adhesive may be used to adhere the lead wire portion 5 to the fixing portion 15. It is also possible to place an O-ring between the lead wire portion 5 and the fixing portion 15. The second tube 1" has a substrate solution flow path 16 adjacent to the fixing portion 15. Thus, the second tube 1" also serves as a holder for the pH electrode 3. The remaining elements are the same as those of the apparatus illustrated in FIG. 1 and denoted by the same symbols as used in FIG. 1.

The upper panel of FIG. 2 shows a cross-sectional view along line A—A.

In the present invention, the subject of the assay is an enzyme that catalyzes a reaction of a substrate to cause a pH change of the substrate solution. The enzymes are present on the surface of the solid bodies such as various organs and solid culture media. Such enzymes include enzymes secreted by microorganisms living on the surface of an organ or on the surface of a solid culture medium, such as urease secreted by *H. pylori*, enzymes expressed on the cell membrane of such microorganisms, and enzymes secreted by various organs. Intracellular enzymes of microorganisms may also be the subject in the present invention, as long as it catalyzes a reaction which causes to change the pH of the reaction solution. According to the present invention, it is possible to detect a microorganism at a targeted site on the solid body surface by assaying an enzyme secreted by the microorganism or an enzyme expressed on the cell membrane of the microorganism.

The substrate solution supplied to the thin tube 1 is a solution containing a substrate of the reaction catalyzed by a subject enzyme to induce pH changes in the solution thereof. The substrate is chosen according to the enzyme to be assayed. Examples of enzyme-substrate combinations include alcohol dehydrogenase/alcohol, glucose oxidase/glucose, catechol oxidase/catechol, NADH peroxidase/NADH, lipase/triacylglycerol, acetyl esterase/acetate, acetylcholine esterase/acetylcholine, gluconolactonase/gluconolactone, alkaline phosphatase/p-nitrophenolphosphoric acid, allyl sulfatase/allyl sulfate and urease/urea.

It is desirable that the substrate solution also serves as a pH electrode washing solution, a pH reference solution for pH measurement, and a salt bridge between the pH electrode and the reference electrode if the pH electrode is far from the reference electrode as shown in FIG. 1. Therefore, the substrate solution desirably has an appropriate pH-buffering capacity and electroconductivity. Such pH-buffering capacity and electroconductivity may be adjusted according to the subject enzyme and the solid body in consideration of actual measuring conditions. When the apparatus of the present invention is used in the human body, the substrate solution is injected into the body; therefore, the substrate solution is preferably free of problems in toxicity and safety.

The assay method using the apparatus of the present invention is described below. Basically, the assay method of the present invention comprises the steps of:

(1) introducing the substrate solution into the thin tube and keeping a constant output potential of pH electrode before assay, (2) bringing the thin tube end opening into contact with a targeted site of the subject solid body surface to form a space between the solid body surface and the inner wall of the thin tube, and introducing the substrate solution into the space to bring the solution into contact with the solid body surface, (3) stopping the supply of the substrate solution, and measuring a pH change of the substrate solution due to substrate reaction on the solid body surface using a pH electrode comprising a tip of a pH-sensing portion that is arranged in the space to be not more than 5 mm away from the thin tube opening.

Figure 3:
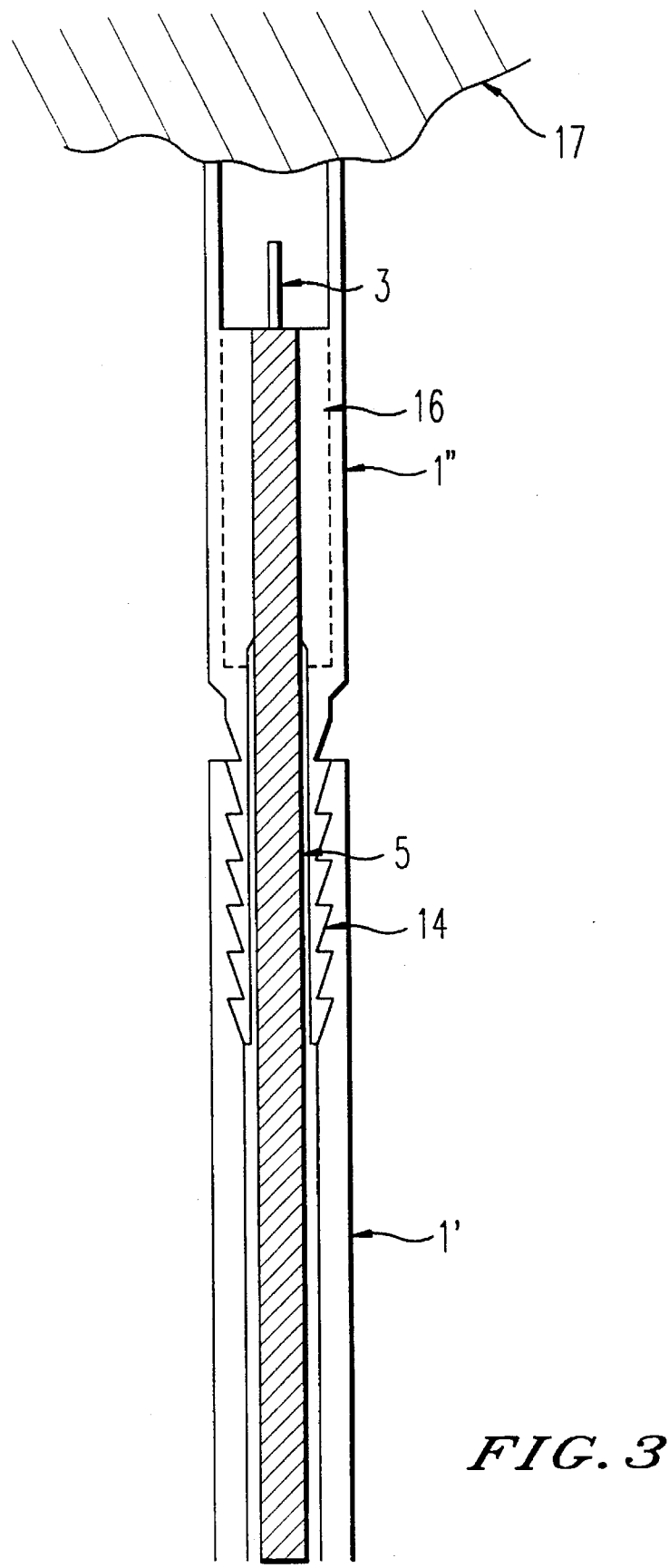
FIG. 3 is a schematic diagram of other preferred embodiment of the apparatus of the present invention which is in use.

Specifically, the liquid supply means 8 operates with the thin tube opening 2 opened in order to supply the substrate solution from the liquid reservoir 9, via the liquid supply tube 7 and adapter 6, into the thin tube 1, and thereby the inside of the thin tube and the pH electrode 3 are washed (see FIG. 1). Then, the output potential of the pH electrode 3 is read as a baseline potential. The liquid supply means 8 is then turned off to stop supplying the substrate solution, and almost simultaneously the thin tube opening 2 is brought into contact with the subject solid body. The space formed between the solid body surface and the inner wall of the thin tube is thus filled with the substrate solution. FIG. 3 depicts the above setting. In this setting, the pH change of the substrate solution is measured. When the subject enzyme is present on the surface of the targeted solid body 17, the substrate in the substrate solution in the space reacts to cause the pH to change in the substrate solution. Then, the pH electrode output potential is read, and the enzyme activity is quantitatively determined on the basis of the potential difference from the baseline potential mentioned above. In order to represent the enzyme activity, some methods can be used, including the method based on the equilibrium value of the above-described potential difference, the method based on the initial rise rate of the above-described potential difference, the method based on the above-described potential difference obtained within a preset period of time, and the method based on the maximum changing rate of the above-described potential difference within a preset period of time. It is also possible to conduct quantitative assay for the amount of enzyme using a calibration curve prepared in advance.

After completion of the assay, the thin tube opening 2 is detached from the solid body surface, and the liquid supply means is again turned on to start supplying the substrate solution from the liquid reservoir to the thin tube. Again, the inside of the thin tube and the pH electrode are washed, and the pH electrode baseline potential is read to prepare for the next assay.

The assay method of the present invention makes it possible to directly assay the subject enzyme at a targeted site on the targeted solid body surface without collecting sample specimens. In addition, the pH of the substrate solution changes according to the amount of enzyme present on the solid body surface, and the enzyme can be assayed qualitatively or quantitatively based upon the pH change. Accordingly, highly reliable results are obtained with high sensitivity. Also, the use of a pH electrode as a detecting means allows rapid and immediate enzyme assay.

Moreover, according to the assay method of the present invention, sequential enzyme assay is possible at a number of sites on a solid body surface, by repeating the above steps (1) through (3), while changing the measuring sites. In clinical situations, sequential assay at different sites can be carried out while monitoring the results of the assay in a diagnostic examination. Therefore, the assay method of the present invention is of particular value.

EXAMPLES

The present invention is hereinafter described in more details by means of the following working examples, but the present invention is not limited by them.

Example (1) Assembly of the apparatus

The apparatus illustrated in FIG. 2 is assembled. The pH electrode 3 is a pH-FET of the entire periphery insulation type produced by the method described on line 7, column 7 through line 6, column 9 in Japanese Patent Examined Publication No. 57-43863, the gate portion of which has tantalum oxide vapor deposition as a pH-sensing membrane. This pH-FET is 5.5 mm long, 0.45 mm wide and 0.15 mm thick and has a gate (pH-sensing face) 0.8 mm away from an end thereof. An about 1.5 mm tip portion is exposed, and the remaining portion is insulated with resin. The first thin tube 1' is a polytetrafluoroethylene tube having an inside diameter of 1.0 mm, an outside diameter of 1.5 mm and a length of 160 cm. The second thin tube 1" of the structure shown in FIG. 2 is made of stainless steel, so that the pH-FET is housed in the tip of the thin tube (first tube 1'). The end opening of the tube 1" has an inside diameter of 1.1 mm, an outside diameter of 1.5 mm that is the same outside diameter as the tube 1', and a total length of 11 mm, including the screw portion 14. The pH-FET is fixed by holding its lead wire portion 5 by the fixing portion 15 with keeping the distance (L) of 0.2 mm between the pH-FET tip and the thin tube opening 2. The reference electrode is a silver-silver chloride liquid junction type reference electrode, and is placed in an adaptor (not illustrated). A pump (not illustrated) which is set to run at a flow rate of 0.5 ml/min is a peristaltic pump. The pH-FET has a pH sensitivity of 58 mV/pH at 25° C. and a mutual conductance of 350 microsiemens. In the following assay, the pH-FET source potential relative to the reference electrode (hereinafter referred to as source potential) is measured as the output potential of the pH-FET.

(2) Assay of urease of H. pylori origin on agar medium

H. pylori NCTC 11637 [Antimicrobial Agents and Chemotherapy, Vol. 37, pp. 769–774 (1993)] is inoculated to Brucella HK agar medium (produced by Kyokuto Pharmaceutical Industry, Co., Ltd.) containing 7% horse serum (produced by Cosmo Bio Company, 801-50), and cultured at 37° C. for 3 days in an atmosphere of a mixed gas consisting of 10% oxygen, 10% carbon dioxide and 80% nitrogen. After the cultivation of H. pylori NCTC 11637, urease on the agar medium (hereinafter referred to as "*H. pylori*-cultured medium") is assayed using the apparatus as assembled in (1) above.

The substrate solution (pH 5.5) contains 155 mM urea, 10 mM ammonium chloride and 154 mM sodium chloride. The substrate solution is supplied to the thin tube for 30 seconds by operating the peristaltic pump. After reaching a stationary state, the pH-FET source potential is memorized in a computer as the baseline potential. The thin tube opening is then brought into contact with the surface of the *H. pylori*-cultured medium, and, at the same time, the peristaltic pump is turned off. Immediately after it, the pH-FET source potential is read at 0.1 second intervals for 30 seconds. A total of 300 readings are memorized in the computer. From these data, the maximum changing rate of pH-FET source potential is calculated. Then, the thin tube opening is detached from the surface of the *H. pylori*-cultured medium to prepare for the next assay.

Next, at two other sites on the surface of the *H. pylori*-cultured medium, the same procedures as above are repeated, and the maximum changing rate of pH-FET source potential is calculated.

Separately, the same procedures as above are also carried out at three sites on the surface of Brucella HK agar medium (produced by Kyokuto Pharmaceutical Industry, Co., Ltd.) containing 7% horse serum (produced by Cosmo Bio Company, 801-50) without *H. pylori* inoculation (hereinafter referred to as "control medium"), and the maximum changing rate of pH-FET source potential is calculated.

As a result, the maximum changing rates of pH-FET source potentials measured at the three sites on *H. pylori*-cultured medium surface are found to be 1.52 mV/sec, 1.60 mV/sec and 2.58 mV/sec, while those on control medium surfaces are found to be 0.25 mV/sec, 0.32 mV/sec and 0.27 mV/sec. There is a distinct difference between *H. pylori*-cultured medium surface and the control medium surface in the maximum changing rate of pH-FET source potential, demonstrating the presence of urease of *H. pylori* origin in the *H. pylori*-cultured medium.

(3) Urease assay on gastric mucosal membrane

Next, urease produced by *H. pylori* living in human gastric ulcer lesions is assayed using the above-described apparatus. First, an endoscope, where the apparatus prepared according to (1) above is incorporated, is inserted into the stomach of each patient. The same substrate solution as used in (2) above is supplied into the thin tube for 30 seconds. When the pH-FET source potential achieves a stationary state, readings of the potential are memorized in the computer as the baseline potential. The thin tube opening is then brought into contact with the inner wall of the fundic gland field, and at the same time the supply of the substrate solution is stopped. The pH-FET source potential is then read at 0.1 second intervals for 30 seconds. A total of 300 readings are memorized in the computer. Then, the thin tube opening is detached from the inner wall of the fundic gland field for the subsequent assay.

From the pH-FET source potential values thus obtained, the maximum changing rate of pH-FET source potential is calculated. Separately, an *H. pylori* culture test is carried out with a mucosal tissue specimen collected from almost the same site where the thin tube opening contacts in the above procedures.

pH-FET source potential values are read on the inner wall of the pyloric gland field according to the same procedures as above, and the maximum changing rate of pH-FET source potential is calculated. An *H. pylori* culture test is also conducted in the same manner as above.

The following procedures comprising the steps of reading pH-FET source potential values on the inner walls of the fundic and pyloric gland fields; calculating the maximum changing rate of pH-FET source potential; and conducting *H. pylori* culture test are carried out on a total of six patients with gastric ulcer.

The maximum changing rates of pH-FET source potential thus obtained and the results of the *H. pylori* culture test are shown in Table 1.

TABLE 1

Comparison of the Results of *H. pylori* Culture Test and the Assay Using the Apparatus of the Present Invention with Gastric Mucosa of the Patients with Gastric Ulcer

| Patient No. | Site of measurement | *H. pylori* culture test | Max. changing rate of pH-FET source potential (mV/sec) |
|---|---|---|---|
| 1 | Fundic gland field | − | −0.125 |
|   | Pyloric gland field | − | −0.079 |
| 2 | Fundic gland field | − | 0.024 |
|   | Pyloric gland field | − | −0.207 |
| 3 | Fundic gland field | − | 0.028 |
|   | Pyloric gland field | − | 0.031 |
| 4 | Fundic gland field | + | 0.539 |
|   | Pyloric gland field | + | 0.425 |
| 5 | Fundic gland field | + | 1.790 |
|   | Pyloric gland field | + | 5.248 |
| 6 | Fundic gland field | + | 2.097 |
|   | Pyloric gland field | + | 4.118 |

+: Positive
−: Negative

In Table 1, the source potential maximum changing rate is calculated by defining the pH shift of the substrate solution toward alkaline direction as a "plus" change.

As is evident from Table 1, the maximum changing rate of the source potential toward alkaline side is not more than 0.1 mV/sec on the gastric mucosal membranes of patients for whom *H. pylori* is not detected by the culture test. On the other hand, patients positive for *H. pylori* show maximum changing rates of not less than 0.4 mV/sec. This suggests that substrate decomposition, i.e., pH shift toward the alkaline direction is small on the gastric mucosal membranes negative for *H. pylori*, because urease derived from *H. pylori* is not present in a detectable amount and that a large amount of urease is present on the mucosal membranes positive for *H. pylori*, causing the pH shift of the substrate solution toward alkaline direction. Table 1 demonstrates that the apparatus and method of the present invention are effective in detecting urease and hence *H. pylori* on the gastric mucosal membrane and in determining the prevalence of *H. pylori*. The maximum potential changing rate sometimes takes negative values on gastric mucosal membranes negative for *H. pylori*. This may be because the pH of the substrate solution in the thin tube tip slightly shifts to the acidic side, being affected by the acidity of the gastric mucosal membrane whose pH is lower than the pH (5.5) of the substrate solution in this test.

Comparative Example

The apparatus is assembled in the same manner as in (1) of the Example above except that the pH-FET is fixed such that the tip of the electrode is kept 6 mm away from the thin tube opening. By the use of this apparatus, urease of *H. pylori* origin on the agar medium or on gastric membrane is assayed according to the procedures as described in (2) or (3) in the Example above.

The maximum changing rates of pH-FET source potential read at 3 sites on the surface of *H. pylori*-cultured medium are 0.24 mV/sec, 0.36 mV/sec and 0.38 mV/sec. On the other hand, those obtained on the control medium are 0.30 mV/sec, 0.26 mV/sec and 0.27 mV/sec. As indicated by these results, there is not distinct difference in the maximum changing rate of pH-FET source potential between the *H. pylori*-cultured medium and the control medium. Therefore, it is impossible to detect the urease of *H. pylori* origin.

The maximum changing rate of pH-FET source potential on gastric membrane is not more than 0.1 mV/sec regardless of the results of *H. pylori* culture test, and, therefore, it is also impossible to detect urease on gastric mucosa.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for assaying urease on a targeted solid body surface comprising:
    (a) contacting an end opening of a thin tube with a targeted solid body surface to form a space between said targeted solid body surface and an inner wall surface of said thin tube;
    (b) supplying a urea solution into said space to bring said urea solution into contact with said targeted solid body surface;
    (c) determining a pH change of said urea solution in said space with a pH electrode, said pH electrode comprising a sensing portion whose tip is arranged in said space to be not more than 5 mm away from said end opening of said thin tube; and
    (d) correlating the pH change determined in step (c) with the presence of urease where an increase in pH indicates the presence of urease.

2. The method according to claim 1, wherein the targeted solid body surface is a surface of a solid body selected from the group consisting of stomach, duodenum, small intestine, large intestine, rectum, urethra, oviduct, bronchium, gingiva, and a solid culture medium.

3. The method according to claim 1, wherein the targeted solid body surface is an inner wall surface of the stomach or the duodenum.

4. The method according to claim 1, wherein the distance between said tip of said sensing portion and said end opening of said thin tube is 0.1 to 1.0 mm.

5. The method according to claim 1, wherein the pH electrode is a pH-sensitive field effect transistor.

6. The method according to claim 1, wherein the thin tube is inserted into an endoscope.

7. The method of claim 1, wherein said space can be filled with said substrate solution.

* * * * *